United States Patent
Dyballa et al.

(10) Patent No.: US 9,650,401 B2
(45) Date of Patent: May 16, 2017

(54) METHOD FOR REDUCING THE CHLORINE CONTENT OF ORGANOBISPHOSPHITES

(71) Applicants: Katrin Marie Dyballa, Recklinghausen (DE); Robert Franke, Marl (DE)

(72) Inventors: Katrin Marie Dyballa, Recklinghausen (DE); Robert Franke, Marl (DE)

(73) Assignee: EVONIK DEGUSSA GMBH, Essen (DE)

(*) Notice: Subject to any disclaimer, the term of this patent is extended or adjusted under 35 U.S.C. 154(b) by 0 days.

(21) Appl. No.: 15/117,894

(22) PCT Filed: Jan. 12, 2015

(86) PCT No.: PCT/EP2015/050385
§ 371 (c)(1),
(2) Date: Aug. 10, 2016

(87) PCT Pub. No.: WO2015/121007
PCT Pub. Date: Aug. 20, 2015

(65) Prior Publication Data
US 2017/0057985 A1    Mar. 2, 2017

(30) Foreign Application Priority Data
Feb. 12, 2014 (DE) .................... 10 2014 202 500

(51) Int. Cl.
C07F 9/6574 (2006.01)
(52) U.S. Cl.
CPC ................ C07F 9/65746 (2013.01)
(58) Field of Classification Search
None
See application file for complete search history.

(56) References Cited

U.S. PATENT DOCUMENTS

| | | | |
|---|---|---|---|
| 6,472,550 B1 | 10/2002 | Toan et al. | |
| 8,003,816 B2 | 8/2011 | Selent et al. | |
| 2007/0219386 A1 | 9/2007 | Ritter | |
| 2008/0076944 A1 | 3/2008 | Bartsch et al. | |
| 2013/0317246 A1 | 11/2013 | Kreidler et al. | |
| 2016/0326197 A1 | 11/2016 | Dyballa et al. | |

FOREIGN PATENT DOCUMENTS

| | | |
|---|---|---|
| CN | 101684130 A | 3/2016 |
| DE | 600 01 533 T2 | 10/2003 |
| DE | 10 2004 049 339 A1 | 4/2006 |
| DE | 10 2006 058 682 A1 | 6/2008 |
| DE | 10 2011 002 640 A1 | 7/2012 |
| EP | 0 285 136 A2 | 10/1988 |
| WO | 2012/095255 A1 | 7/2012 |
| WO | 2013/098368 A1 | 7/2013 |
| WO | 2015113840 A1 | 8/2015 |
| WO | 2015121007 A1 | 8/2015 |
| WO | 2015176927 A1 | 11/2015 |
| WO | 2015176929 A1 | 11/2015 |

OTHER PUBLICATIONS

International Search Report for PCT/EP2015/050385, dated Mar. 31, 2015 in English and German Language.
Armarego, Wilfred L.F., et al. Purification of Laboratory Chemicals, Butterworth Heinemann (Elsevier), 6th edition, Oxford 2009 (index and chapter abstracts provided).
Harris, Robin K. et al. NMR Nomenclature, Nuclear Spin Properties and Conventions for Chemical Shifts. Pure Appl. Chem., 2001, 73, pp. 1795-1818.
Harris, Robin K. et al. Further Conventions for NMR Shielding and Chemical Shifts. Pure Appl. Chem, 2008, 80, pp. 59-84.
Written Opinion of the International Searching Authority for PCT/EP2015/050385 dated Aug. 20, 2015 (11 pages—German with English Translation).
International Preliminary Report on Patentability for PCT/EP2014/050385 dated Aug. 16, 2016 (13 pages—German with English Translation).
International Search Report for DE 10 2014 202.500.1 dated Sep. 23, 2014 (6 pages).
Organikum: Organisch-Chemisches Grundpraktium, A. Einfuhyung in die laboratoriumstechnik, 18, 1990, pp. 30-34.

*Primary Examiner* — Michael Barker
(74) *Attorney, Agent, or Firm* — Smith, Gambrell & Russell, LLP

(57) ABSTRACT

The invention relates to a universally usable process for reducing the chlorine content of organobisphosphites.

14 Claims, No Drawings

METHOD FOR REDUCING THE CHLORINE CONTENT OF ORGANOBISPHOSPHITES

The invention relates to a universally usable process for reducing the chlorine content of organobisphosphites.

Organophosphorus compounds have gained considerable industrial significance because of their wide range of use. They are used directly as plasticizers, flame retardants, UV stabilizers or as antioxidants. In addition, they are important intermediates in the production of fungicides, herbicides, insecticides and pharmaceuticals.

A specific field of use of the organophosphorus compounds is catalysis:

For instance, especially phosphines, phosphites and phosphoramidites are used as ligands in catalyst complexes which are used in turn for homogeneous catalysis of processes operated on the industrial scale. Particular mention should be made of the hydroformylation of unsaturated compounds with carbon monoxide and hydrogen, which is generally effected in the presence of a homogeneous catalyst system including a metal and at least one organophosphorus compound as ligand.

An introduction into homogeneously catalysed hydroformylation is given by: B. CORNILS, W. A. HERRMANN, Applied Homogeneous Catalysis with Organometallic Compounds, vol. 1 & 2, VCH, Weinheim, N.Y., 1996; R. Franke, D. Selent, A. Börner, Applied Hydroformylation, Chem. Rev., 2012, DOI:10.1021/cr3001803.

The synthesis of phosphorus ligands is described repeatedly in the literature. A good overview can be found in: "Phosphorus(III) Ligands in Homogeneous Catalysis—Design and Synthesis" by Paul C. J. Kamer and Piet W. N. M. van Leeuwen; John Wiley and Sons, 2012.

In the synthesis of these ligands, chlorinated reagents are frequently used. For instance, in the synthesis of phosphite ligands, phosphorus trichloride ($PCl_3$) is usually used.

The chlorine compounds used in the preparation of organophosphorus compounds present many difficulties in the proper use or further processing of the organophosphorus compound:

For instance, the desired organophosphorus compound is never obtained in pure form immediately, and is always obtained in contaminated form as an organophosphorus product which, as well as the organophosphorus compound desired, also contains impurities. The impurities are unconverted or incompletely converted reagents, auxiliaries or products from side reactions. In this context, impurities in the form of chlorine compounds present particular difficulties:

If the chlorinated impurities get into a steel pressure reactor together with the organophosphorus compound used as ligand, the pressure reactor is subject to elevated corrosion as a result of the chloride. This is especially true of continuous processes, in which the organophosphorus compounds are metered in over the course of the reaction. This is the case, for example, when the organophosphorus compound is used as a ligand in industrial scale hydroformylation. The metered addition inevitably also results in an accumulation of the secondary components in the reactor. This is critical especially when chloride is one of the secondary components, since chloride attacks even stainless steels (cf. Merkblatt 893 "Edelstahl rostfrei für die Wasserwirtschaft" [Information Sheet 893 "Corrosion-Free Stainless Steel for Water Management"], 1st edition 2007, publisher: Informationsstelle Edelstahl Rostfrei, Düsseldorf.)

In the presence of chloride ions, there is a particular risk of stress-cracking corrosion, which can lead in more favourable cases to a premature shutdown of the process and to a reactor overhaul, but in less favourable cases even to rupture of the reactor. it is therefore of overriding importance to prevent entrainment of chlorinated compounds via the organophosphorus catalyst system.

An important class of organophosphorus compounds is that of the organobisphosphites, or bisphosphites for short.

These play a major role in hydroformylation (see R. Franke, D. Selent, A. Börner: Applied Hydroformylation. Chem. Rev., 2012, DOI:10.1021/cr3001803).

It is therefore important to develop a preparation and purification process for organobisphosphites, which provides the corresponding ligands with a low chloride content. This process should be applicable to a maximum number of organobisphosphites, since the chlorine problem plays a fundamental role for any ligand before it can be used in an industrial scale plant.

The chloride content can be determined analytically in a simple manner, for example by aqueous titration. A more extensive determination is that of the total chlorine content, which, as well as the chlorides, also encompasses chlorine bound in other forms. Emphasis on the total chlorine content is also of material relevance, in that it cannot be ruled out that chlorine bound in another form is also able to damage the reactor. In judging the limits for total chlorine, however, the chloride content remains crucial.

A suitable method for determining the total chlorine content is the combustion according to Wickbold with sample preparation to DIN 51408 and analysis by ion chromatography to DIN EN ISO 10304.

The patent literature discloses various methods for reducing the total chlorine content of organophosphorus ligands after the actual synthesis:

DE 10 2011 002 640 A1 discloses a process for purifying biphephos (6,6'-[(3,3'-di-tert-butyl-5,5'-dimethoxy-1,1'-biphenyl-2,2'-diyl)bis(oxy)]bis(dibenzo[d,f][1,3,2]dioxaphosphepine)). The process described therein is intended to reduce the chlorine content of biphephos. This is done by washing the biphephos with a solvent selected from ethyl acetate, anisole, ortho-xylene, toluene, acetone, 2-propanol and $C_5$-$C_{10}$-alkanes, or recrystallizing from such a solvent.

In this context, however, the long period needed to precipitate or crystallize the product is in need of improvement. The ligand is precipitated overnight, meaning that >8 hours are required. Moreover, it is pointed out in the examples that another solvent has to be added after the precipitation overnight, in order to complement the precipitation (Example 2). These long reaction times are problematic in industrial scale syntheses, since the effect of long residence times and hence ultimately long production times for the ligand is to increase the cost thereof.

Document EP 0 285 136 claims a process for purifying tertiary organophosphites of pentavalent organophosphorus compounds which form as by-products of the synthesis and also as degradation or hydrolysis products of the tertiary organophosphites. The process envisages the treatment of the dissolved contaminated organophosphite with water at elevated temperature in the presence of a Lewis base. Lewis bases used are inorganic salts (carbonates, hydroxides, oxides), tertiary amines and polymers that bear amine groups.

One disadvantage of the process claimed lies in the treatment with water. Not only the impurities to be removed but also the tertiary organophosphites themselves react under the conditions specified, such that a portion of the product of value is lost according to the hydrolysis stability of the organophosphites.

Document DE 10 2004 049 339 describes a process for purifying phosphorus chelate ligands by means of extraction using a polar extractant. The crude ligand was extracted here six times with a polar solvent, and has a content of amine base, amine hydrochloride or mixtures thereof of less than 100 ppm thereafter. In this method of purification, however, enormous amounts of solvent are needed, which is in need of improvement from an economic and ecological point of view.

CN 101684130 A discloses the purification of phosphite ligands through the addition of deionized water and subsequent extraction. The organic solvent is removed by distillation in a subsequent step, and the crude product is recrystallized again. In this way, it was possible to obtain a product having a residual chlorine content of 0.01% by weight of chlorine.

In order to reduce the chlorine content of the ligand by this method, an extraction and a subsequent recrystallization are thus necessary. This means that a large amount of solvent has to be used, and yield losses because of the various purification steps and the possible lack of hydrolysis stability of the organophosphites a portion of the product of value to be lost.

It was thus an object of the present invention to develop a purifying process for organobisphosphites, in which the chlorine content is reduced, without this process having the above-described disadvantages.

A particular object was for the process to purify organobisphosphites having a chlorine content of 1500 ppm to 100 000 ppm in the organobisphosphite to a chlorine content of less than 350 ppm in the organobisphosphites. Preferably, the chlorine content was to be reduced to less than 300 ppm in the organobisphosphite, and more preferably to less than 200 ppm in the organobisphosphite. The chlorine contents reported are meant as total chlorine contents.

This is because the contaminated organobisphosphite can contain organic chlorides and/or inorganic chlorides. Organic chlorides contain at least one carbon atom, whereas inorganic chlorides do not include any carbon. Contamination of the organophosphorus product by the following chlorides is particularly likely, since these chlorine compounds are either required in the course of synthesis of organophosphorus compounds or are unavoidably by-produced:

phosphorus trichloride, chlorophosphites, dichlorophosphites, hydrochlorides of amines, hydrochlorides of alkali metals, chlorides of alkaline earth metals, chlorine acids obtainable from the hydrolysis of phosphorus trichloride.

Therefore, the contaminated organobisphosphite generally includes at least one of the chlorides enumerated.

In addition, the purifying process should dispense with the use of water because of the lack of hydrolysis stability of the organobisphosphites.

This object is achieved by a process according to claim 1.

Process for reducing the chlorine content in an organobisphosphite of one of the general formulae I, II, III, IV, V and VI:

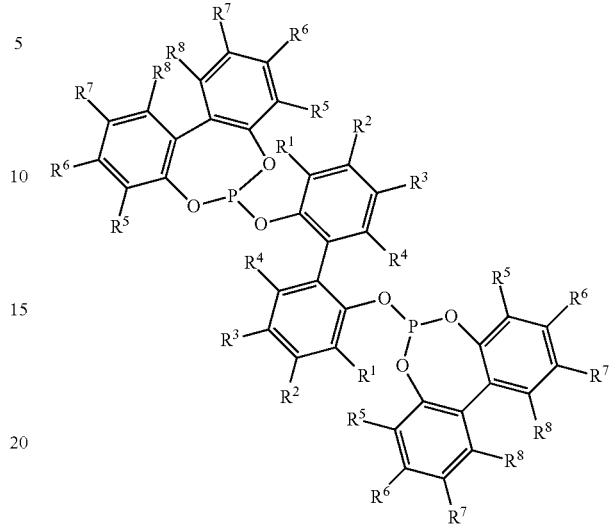

(I)

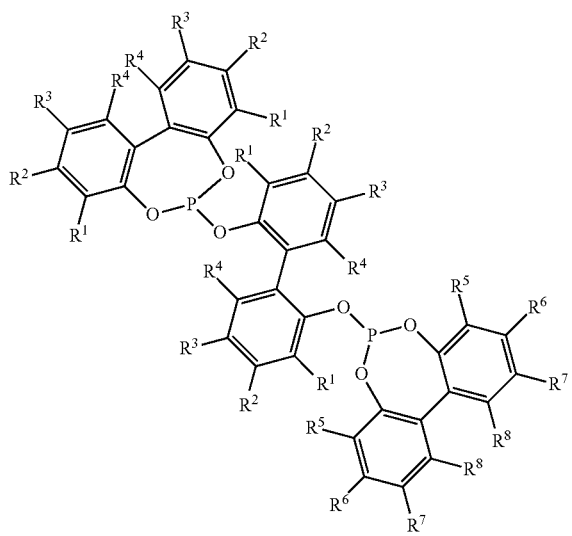

(II)

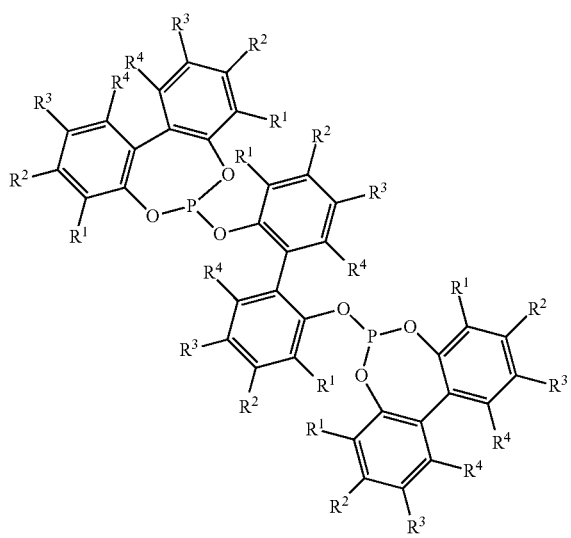

(III)

-continued

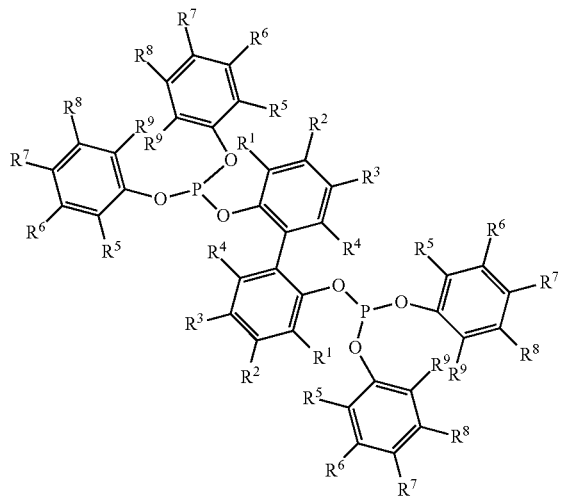
(IV)

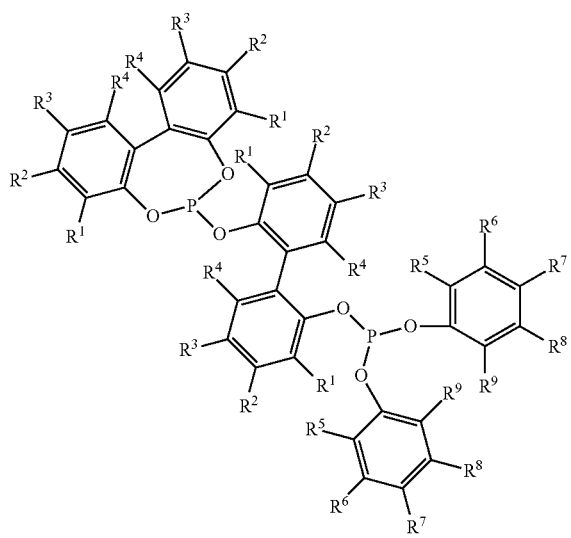
(V)

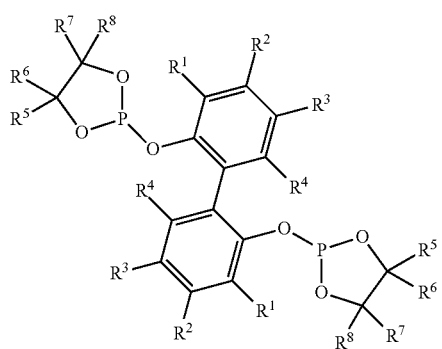
(VI)

where $R^1$, $R^2$, $R^3$, $R^4$, $R^5$, $R^6$, $R^7$, $R^8$, $R^9$ are each independently selected from: —H, —($C_1$-$C_{12}$)-alkyl, —O—($C_1$-$C_{12}$)-alkyl, —O—($C_6$-$C_{20}$)-aryl, —($C_6$-$C_{20}$)-aryl, halogen, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$;

and the four following pairs of radicals are not both the same radical in all four pairs:
$R^1$ and $R^5$, $R^2$ and $R^6$, $R^3$ and $R^7$, $R^4$ and $R^8$;
comprising the process steps of:
a) partly or fully dissolving the organobisphosphite in a first solution,
b) introducing the first solution into a second solution, which results in precipitation of the purified organobisphosphite,
where
the first solution comprises a first solvent and a first base,
the second solution comprises a second solvent and a second base,
and
the first solvent is selected from:
aromatics, alcohols, acetone, ethyl acetate, acetonitrile, ethers,
the second solvent is selected from:
aromatics, C5-C10-alkanes, alcohols, acetone, ethyl acetate, acetonitrile, ethers,
the first base is selected from:
amine bases, alkoxides, pyridine, pyridine derivatives, N-methyl-2-pyrrolidone, triethanolamine,
the second base is selected from:
amine bases, alkoxides, pyridine, pyridine derivatives, N-methyl-2-pyrrolidone, triethanolamine, and the organobisphosphite has better solubility in the first solvent than in the second solvent.

Of the four radical pairs $R^1$ and $R^5$, $R^2$ and $R^6$, $R^3$ and $R^7$, $R^4$ and $R^8$, up to 3 pairs may each be the same radical as pairs, provided that the two radicals in the remaining pair are not the same.

For example, the following radical combinations are possible:
$R^1$=$R^5$, $R^2$=$R^6$, $R^3$=$R^7$, $R^4$ and $R^8$ are different or
$R^1$ and $R^5$ are different, $R^2$=$R^6$, $R^3$=$R^7$, $R^4$=$R^8$ or
$R^1$ and $R^5$ are different, $R^2$=$R^6$, $R^3$=$R^7$, $R^4$ and $R^8$ are different or
$R^1$ and $R^5$ are different, $R^2$ and $R^6$ are different, $R^3$ and $R^7$ are different, $R^4$ and $R^8$ are different.

The only radical combination ruled out is as follows:
$R^1$=$R^5$, $R^2$=$R^6$, $R^3$=$R^7$, $R^4$=$R^8$.

The result of the prerequisite that the organobisphosphite has better solubility in the first solvent than in the second solvent is that the first solvent cannot be identical to the second solvent.

($C_1$-$C_{12}$)-Alkyl and O—($C_1$-$C_{12}$)-alkyl may each be unsubstituted or substituted by one or more identical or different radicals selected from ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

($C_3$-$C_{12}$)-Cycloalkyl and ($C_3$-$C_{12}$)-heterocycloalkyl may each be unsubstituted or substituted by one or more identical or different radicals selected from ($C_1$-$C_{12}$)-alkyl, ($C_1$-$C_{12}$)-alkoxy, ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

($C_6$-$C_{20}$)-Aryl may each be unsubstituted or substituted by one or more identical or different radicals selected from ($C_1$-$C_{12}$)-alkyl, ($C_1$-$C_{12}$)-alkoxy, ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

In the context of the invention, the expression —($C_1$-$C_{12}$)-alkyl encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of —($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression —$(C_1-C_{12})$-alkyl also apply to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted —$(C_1-C_{12})$-alkyl groups and substituted —$(C_1-C_{12})$-alkoxy groups may have one or more substituents, depending on their chain length. The substituents are preferably each independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl.

The expression "—$(C_3-C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbonyl or adamantyl.

The expression "—$(C_3-C_{12})$-heterocycloalkyl groups", in the context of the present invention, encompasses nonaromatic saturated or partly unsaturated cycloaliphatic groups having 3 to 12, especially 5 to 12, carbon atoms. The —$(C_3-C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —$(C_3-C_{12})$-heterocycloalkyl groups tetrahydrothiophenyl, tetrahydrofuryl, tetrahydropyranyl and dioxanyl.

Substituted —$(C_3-C_{12})$-cycloalkyl groups and substituted —$(C_3-C_{12})$-heterocycloalkyl groups may have one or more (e.g. 1, 2, 3, 4 or 5) further substituents, depending on their ring size. These substituents are preferably each independently selected from —$(C_1-C_{12})$-alkyl, —$(C_1-C_{12})$-alkoxy, —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl. Substituted —$(C_3-C_{12})$-cycloalkyl groups preferably bear one or more —$(C_1-C_6)$-alkyl groups. Substituted —$(C_3-C_{12})$-heterocycloalkyl groups preferably bear one or more —$(C_1-C_6)$-alkyl groups.

In the context of the present invention, the expression "—$(C_6-C_{20})$-aryl" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6-C_{10})$-aryl. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —$(C_6-C_{20})$-aryl groups may have one or more (e.g. 1, 2, 3, 4 or 5) substituents, depending on the ring size. These substituents are preferably each independently selected from —$(C_1-C_{12})$-alkyl, —$(C_1-C_{12})$-alkoxy, —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl.

Substituted —$(C_6-C_{20})$-aryl groups are preferably substituted —$(C_6-C_{10})$-aryl groups, especially substituted phenyl or substituted naphthyl or substituted anthracenyl. Substituted —$(C_6-C_{20})$-aryl groups preferably bear one or more, for example 1, 2, 3, 4 or 5, substituents selected from —$(C_1-C_{12})$-alkyl groups, —$(C_1-C_{12})$-alkoxy groups.

In one variant of the process, the first solvent is selected from: ethyl acetate, anisole, ortho-xylene, toluene. acetone, methanol, ethanol, propanol, isopropanol, acetonitrile.

Preferably, the first solvent is selected from: ethyl acetate, anisole, ortho-xylene, toluene.

More preferably, the first solvent is selected from: ortho-xylene, toluene.

In one variant of the process, the second solvent is selected from:
ethyl acetate, anisole, ortho-xylene, toluene. acetone, methanol, ethanol, propanol, isopropanol, acetonitrile, tetrahydrofuran, diethyl ether, glycol, C5-C10-alkanes.

Preferably, the second solvent is selected from: ethyl acetate, acetone, methanol, ethanol, propanol, isopropanol, acetonitrile, C5-C10-alkanes.

More preferably, the second solvent is acetonitrile.

C5-C10-Alkanes are especially pentane, hexane, n-heptane, octane, nonane and decane. Among the alkanes, n-heptane is preferred.

In one variant of the process, the first base is selected from: triethylamine, dimethylaminobutane (DMAB), pentylamine, hexylamine, dibutylamine, N-methyl-2-pyrrolidone (NMP), triethanolamine, sodium methoxide, sodium ethoxide, pyridine, dimethylaminopyridine (DMAP).

Preferably, the first base is selected from: triethylamine, dimethylaminobutane (DMAB), sodium methoxide, sodium ethoxide, pyridine, dimethylaminopyridine (DMAP).

More preferably, the first base is dimethylaminobutane (DMAB).

In one variant of the process, the second base is selected from: triethylamine, dimethylaminobutane (DMAB), pentylamine, hexylamine, dibutylamine, N-methyl-2-pyrrolidone (NMP), triethanolamine, sodium methoxide, sodium ethoxide, pyridine, dimethylaminopyridine (DMAP).

Preferably, the second base is selected from: triethylamine, dimethylaminobutane (DMAB), sodium methoxide, sodium ethoxide, pyridine, dimethylaminopyridine (DMAP).

More preferably, the second base is dimethylaminobutane (DMAB).

In one variant of the process, the second solution comprises a third solvent non-identical to the second solvent.

The third solvent may, though, be identical to the first solvent.

In one variant of the process, the third solvent is identical to the first solvent.

In one variant of the process, the second solution comprises a third solvent non-identical to the second solvent, and the third solvent is selected from:
aromatics, alcohols, acetone, ethyl acetate, acetonitrile, ethers.

In one variant of the process, in process step a), the organobisphosphite is dissolved fully in the first solution.

In one variant of the process, the introduction in process step b) is effected by means of dropwise addition.

In another variant of the process, the introduction in process step b) is effected by means of metered addition.

In one variant of the process, the first base and the second base are not the same base.

In a particularly preferred variant of the process, the first base and the second base are the same base.

In a preferred embodiment of the process according to the invention, the organobisphosphite is dissolved in the first solvent, preferably while heating, insoluble constituents are removed by filtration (by what is called a clarifying filtration, optionally also with addition of a filtering aid), preferably at a temperature of up to 130° C., and the organobisphosphite is subsequently metered into the second solvent while warm, such that the organobisphosphite precipitates out or crystallizes out.

Filtration aids used may be either mineral filtration aids, for example silicon dioxide, or organic filtration aids, for example cellulose or activated carbon. It is also possible to mix different filtration aids.

In one variant of the process, the organobisphosphite has a chlorine content of 1500 ppm to 100 000 ppm on introduction in process step b).

Preferably, the organobisphosphite has a chlorine content of 5000 ppm to 100 000 ppm on introduction in process step b).

The chlorine contents reported are meant as total chlorine contents.

The total chlorine content is determined according to Wickbold: sample preparation to DIN 51408 and analysis by ion chromatography to DIN EN ISO 10304.

In one variant of the process, the second solution is heated to a temperature in the range from −20° C. to 120° C. before the first solution is introduced into the second solution in process step b). The temperature of the solvent should be chosen here such that it does not boil. The temperature thus depends on the choice of solvent.

Preferably, the second solution is heated to a temperature in the range from −10° C. to 80° C. before the first solution is introduced into the second solution in process step b).

In one variant of the process for reducing the chlorine content, an organobisphosphite of one of the general formulae I, II, IV and VI:

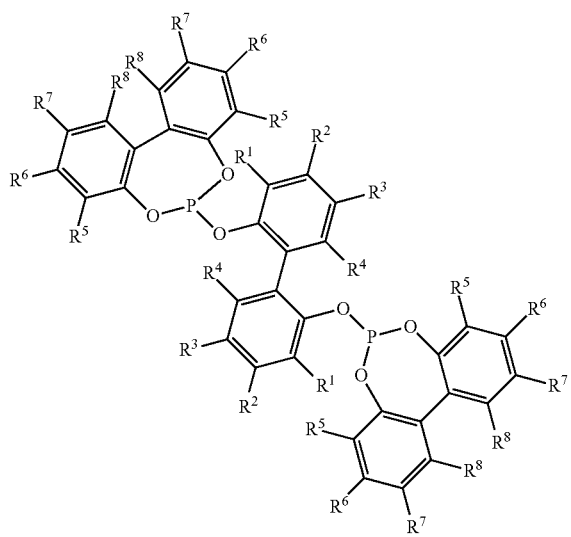
(I)

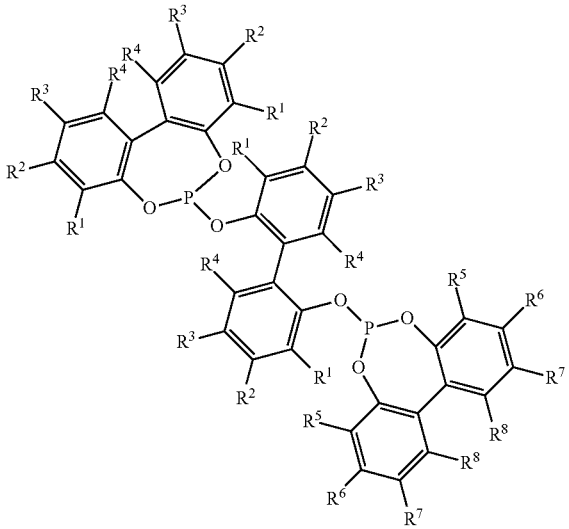
(II)

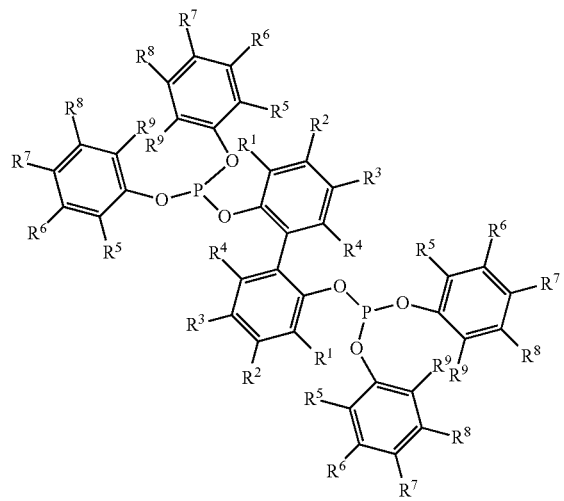
(IV)

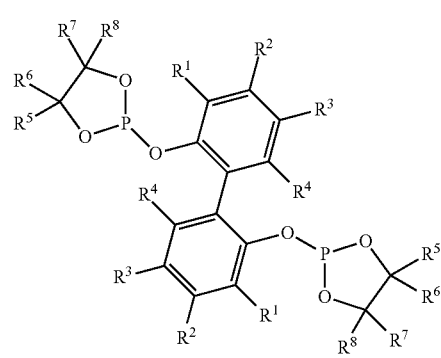
(VI)

is purified, where the radicals are each as defined above.

In one variant of the process for reducing the chlorine content, an organobisphosphite of one of the general formulae I, II and VI:

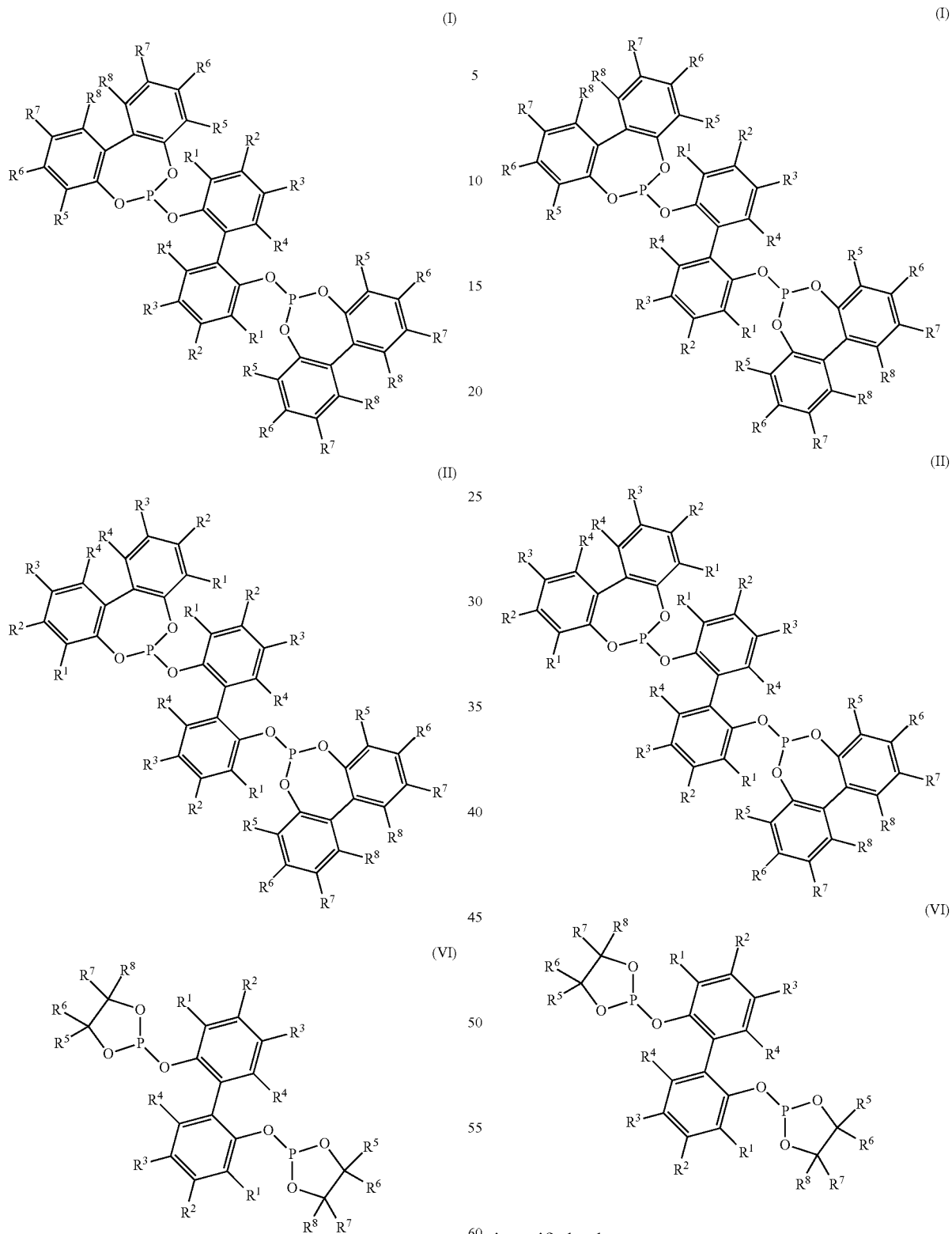

is purified, where the definition of the radical corresponds to the definition given above.

In one variant of the process for reducing the chlorine content, an organobisphosphite of one of the general formulae I, II and VI:

is purified, where $R^1$, $R^2$, $R^3$, $R^4$, $R^5$, $R^6$, $R^7$, $R^8$ are each independently selected from: —H, —($C_1$-$C_{12}$)-alkyl, —O—($C_1$-$C_{12}$)-alkyl, —O—($C_6$-$C_{20}$)-aryl, —($C_6$-$C_{20}$)-aryl.

More preferably, the process according to the invention serves to purify bisphosphites of one of the structural formulae (Ia), (Ib), (Ic), (IIa) and (VIa):

(Ia)
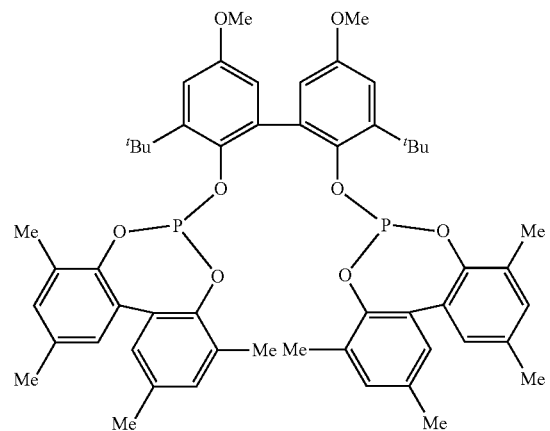

(Ib)
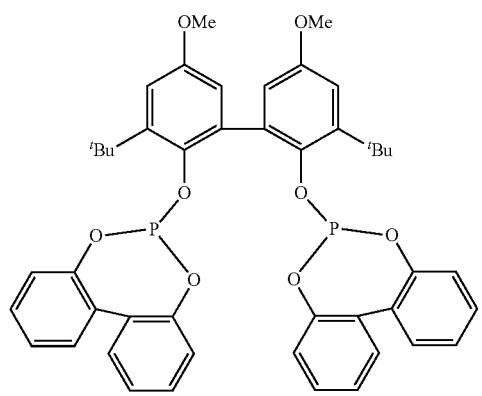

(Ic)
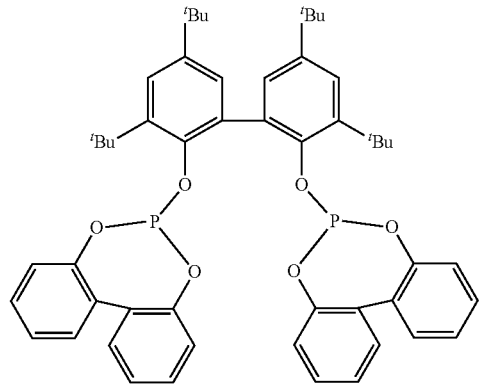

(IIa)
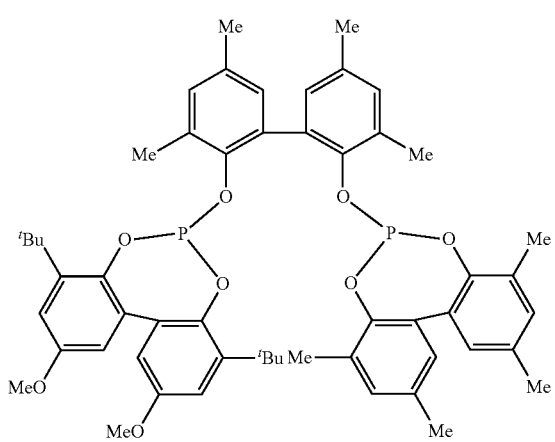

(VIa)
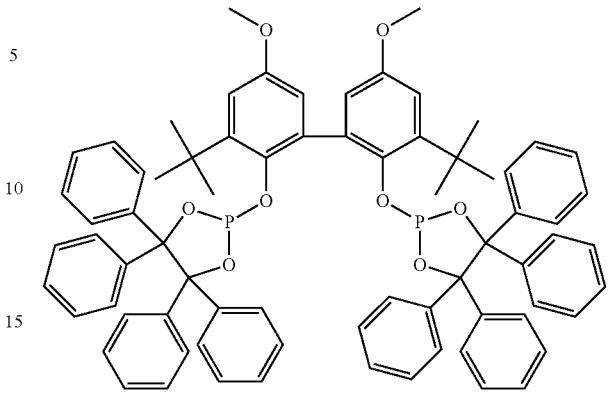

The process claimed may also have upstream process steps, for example the synthesis of the ligands. In that case, these process steps are effected prior to process step a).

In one variant of the process, the following process steps are included upstream of process step a):

i) reacting a diol of the general formula (VII):

(VII)
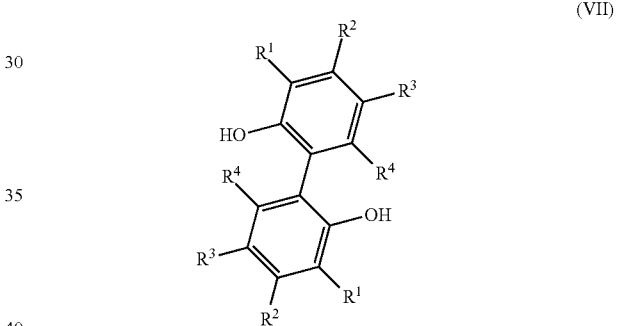

where $R^1$, $R^2$, $R^3$, $R^4$ are each independently selected from: —H, —($C_1$-$C_{12}$)-alkyl, —O—($C_1$-$C_{12}$)-alkyl, —O—($C_6$-$C_{20}$)-aryl, —($C_6$-$C_{20}$)-aryl, halogen, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH—$SO_3H$, —$SO_3Na$, —$NO_2$, —CN, —$NH_2$, —N[($C_1$-$C_{12}$)-alkyl]$_2$;

with $PCl_3$ to give the phosphorochloridite derivative under inert gas atmosphere;

ii) reacting the phophorochloridite derivative from i) with a mono- or dialcohol in a fourth solvent.

Stages i) and ii) can be effected here with addition of a base.

In one variant of the process, the fourth solvent from process step ii) corresponds to the second solvent.

After recrystallization, the organobisphosphite can be isolated. This is typically accomplished by filtering off and, optionally, drying the filtered-off organobisphosphite.

As well as the process, the use of the product obtained by this process in a hydroformylation reaction is also claimed. The product here functions as a ligand in a catalyst complex composed of the ligand and at least one central metal atom. This catalyst complex is used for catalysis of a hydroformylation reaction.

Use of an organobisphosphite of one of the general formulae I, II, III, IV, V and VI which has been purified by a process according to any of claims 1 to 11 as ligands in a catalyst complex which catalyses a hydroformylation reaction.

The invention is to be illustrated in detail hereinafter by working examples.

It is particularly advantageous that particular solvent combinations which result from the ligand synthesis (acetonitrile (ACN), N,N'-dimethylaminobutane (DMAB)) can be used for recrystallization after a single distillation.

This allows reuse of the mixture used from the synthesis, which is advantageous from an ecological and economic point of view.

This is therefore a particularly simple and efficient process. In this context, it is also particularly advantageous that this process is performable very rapidly, meaning that the purified organobisphosphite precipitates out or crystallizes out again after a short reaction time, and the process thus has good space-time yields. This is advantageous especially for a synthesis on the industrial scale, since prolonged reaction times directly affect the cost of the compound. The good possibility of industrial scale use is an important criterion, since the preparation complexity and the associated costs that arise may only be so high that the viability of the overall process is still assured.

GENERAL WORKING METHODS

The total chlorine content reported in connection with this invention is determined according to Wickbold: sample preparation to DIN 51408 and analysis by ion chromatography to DIN EN ISO 10304.

All the preparations which follow were conducted with standard Schlenk vessel technology under protective gas. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

The products were characterized by means of NMR spectroscopy. Chemical shifts are reported in ppm.

The $^{31}$P NMR signals were referenced according to: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). The chlorine determination was effected in the form of combustion according to Wickbold: sample preparation to DIN 51408 and analysis by ion chromatography to DIN EN ISO 10304.

Synthesis of (1):

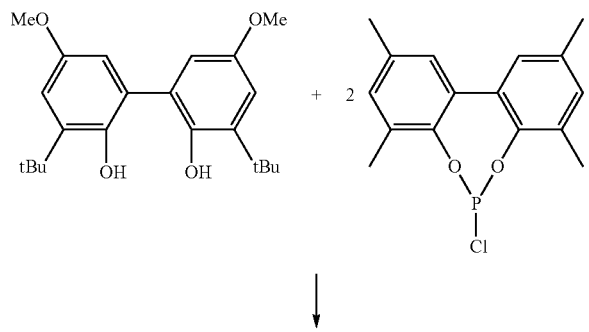

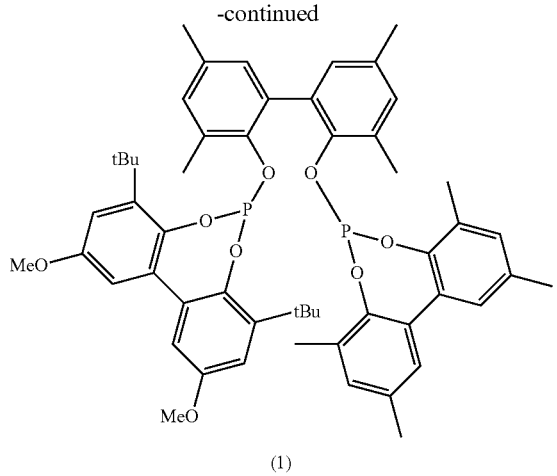

(1)

The target product (1) will be referred to hereinafter, inter alia, as crude ligand or crude material.

Preparation of the Crude Material

In a 100 ml Schlenk vessel, under protective gas, 6 g (19.0 mmol) of 2,2'-bis(3,5-dimethylphenyl) chlorophosphite were dissolved in 20 ml of degassed acetonitrile (ACN) and heated to 35° C. In a second Schlenk vessel (50 ml), 3.4 g (9.0 mmol) of 3,3'-di-tert-butyl-5,5'-dimethoxy-[1,1'-biphenyl]-2,2'-diol were dissolved in 15 ml of dimethylaminobutane (DMAB) and then slowly added dropwise to the chlorophosphite solution. The reaction was left to stir at 35° C. overnight.

The next day, the solution was filtered and the solids were washed twice with ACN. The target product was obtained as a white solid (5.3 g, 66%). $^{31}$P NMR (202.4 MHz, toluene-d$^8$): 142.8 and 141.2 (89.4%) and further impurities. Cl value: according to Wickbold 0.44% by mass.

Purification of the Crude Material

The purification processes according to the invention are identified by *.

1) Toluene/Acetonitrile

In a 500 ml Schlenk vessel which had been repeatedly evacuated and filled with inert gas, 10 g of crude ligand were dissolved in 40 ml of degassed toluene at 105° C. while stirring.

A second 500 ml Schlenk vessel which had been repeatedly evacuated and filled with inert gas was initially charged with 200 ml of degassed acetonitrile. Then the still-warm ligand/toluene solution was cautiously and gradually added dropwise to the acetonitrile at room temperature (RT) while stirring within about 10 min. No exothermicity was detected, but immediate precipitation of solids was apparent. The solids obtained were stirred at RT for another 2 h, then filtered, washed through once with 25 ml of degassed acetonitrile, dried. The product was obtained in 88% yield (8.8 g).

Chlorine result according to Wickbold: 430 ppm

2) Toluene/Acetonitrile-Triethylamine

In a 500 ml Schlenk vessel which had been repeatedly evacuated and filled with inert gas, 10 g of crude ligand were dissolved in 40 ml of degassed toluene at 105° C. while stirring. Then the solution was cooled again to 20° C.

A second 500 ml Schlenk vessel which had been repeatedly evacuated and filled with inert gas was initially charged with 200 ml of degassed acetonitrile and 20 ml of triethylamine while stirring. Then the mixture was likewise cooled to 20° C. Thereafter, the ligand/toluene solution was cautiously and gradually added dropwise to the degassed acetonitrile/triethylamine solution at 20° C. while stirring within about 15 min. The precipitation of solids was perceived after about 3 min. The solids obtained were stirred at RT for another 2 h, then filtered, washed through once with 25 ml of degassed acetonitrile, dried. The product was obtained in 89% yield (8.9 g).

Chlorine result according to Wickbold: 400 ppm

3) Toluene/Acetonitrile-DMAB

In a 500 ml Schlenk vessel which had been repeatedly evacuated and filled with inert gas, 10 g of crude ligand were dissolved in 40 ml of degassed toluene at 105° C. while stirring. Then the solution was cooled again to 20° C.

A second 500 ml Schlenk vessel which had been repeatedly evacuated and filled with inert gas was initially charged with 200 ml of degassed acetonitrile and 20 ml of N,N'-dimethylaminobutane (DMAB) while stirring. Then the mixture was likewise cooled to 20° C. Thereafter, the ligand/toluene solution was cautiously and gradually added dropwise to the degassed acetonitrile/DMAB solution at 20° C. while stirring within about 15 min. The precipitation of solids was perceived after about 3 min. The solids obtained were stirred at RT for another 2 h, then filtered, washed through once with 25 ml of degassed acetonitrile, dried and introduced into a glovebox. The product was obtained in 89% yield (8.89 g).

Chlorine result according to Wickbold: 350 ppm

4) Toluene-Triethanolamine/Acetonitrile

In a 500 ml Schlenk vessel which had been repeatedly evacuated and filled with inert gas, 10 g of crude ligand were dissolved in 40 ml of degassed toluene and 10 ml of degassed triethanolamine at 105° C. while stirring. Then the solution was cooled again to 20° C.

A second 500 ml Schlenk vessel which had been repeatedly evacuated and filled with inert gas was initially charged with 200 ml of degassed ACN while stirring. Then it was cooled to RT. Thereafter, the ligand/toluene/amine solution was cautiously and gradually added dropwise to the degassed ACN at 20° C. while stirring within about 15 min. The precipitation of solids was perceived after about 3 min. The solids obtained were stirred at RT for another 2 h, then filtered, washed through once with 25 ml of degassed acetonitrile, dried. The product was obtained in 91% yield (9.1 g).

Chlorine result according to Wickbold: 800 ppm

5) Toluene-Triethanolamine/Ethyl Acetate

In a 500 ml Schlenk vessel which had been repeatedly evacuated and filled with inert gas, 20 g of crude ligand were dissolved in 90 ml of degassed toluene and 15 ml of triethanolamine at 105° C. while stirring. In the course of cooling, a 2nd phase separated out, which mixed in again when stirred.

Then the solution was cooled again to RT.

A second 500 ml Schlenk vessel which had been repeatedly evacuated and filled with inert gas was initially charged with 300 ml of degassed ethyl acetate while stirring.

Thereafter, the ligand/toluene/amine solution was cautiously and gradually added dropwise to the degassed ethyl acetate solution at 20° C. while stirring within about 30 min.

The precipitation of small amounts of solids was perceived after about 2 h. After 3 h, precipitation still did not appear to be complete. To improve the precipitation, 100 ml of ethyl acetate were added and the mixture was stirred for a further 30 min.

Subsequently filtered, washed once with 25 ml of degassed acetonitrile, dried. The product was obtained in 28% yield (5.57 g).

Chlorine result according to Wickbold: 0.74%/0.65% by weight

6) Toluene/EtOH-Triethanolamine

In a 500 ml Schlenk vessel which had been repeatedly evacuated and filled with inert gas, 10 g of crude ligand were dissolved in 40 ml of degassed toluene at 105° C. while stirring. Then the solution was cooled again to 20° C. A second 500 ml Schlenk vessel which had been repeatedly evacuated and filled with inert gas was initially charged with 150 ml of degassed methanol and 15 ml of degassed triethanolamine while stirring. Then the mixture was likewise cooled to 20° C. Thereafter, the ligand/toluene solution was cautiously and gradually added dropwise to the degassed methanol/triethanolamine solution at 20° C. while stirring within about 1 h. The precipitation of solids was perceived after about 3 min. The solids obtained were stirred at RT for another 2 h, then filtered, washed through twice with 25 ml of degassed acetone, dried. The product was obtained in 91% yield (9.1 g).

Chlorine result according to Wickbold: 340 ppm

7) Toluene-DMAB/n-Heptane

In a 500 ml Schlenk vessel which had been repeatedly evacuated and filled with inert gas, 10 g of crude ligand were dissolved in 45 ml of degassed toluene and 7.5 ml of degassed N,N'-dimethylaminobutane at 105° C. while stirring (a solution was obtained within 15 min).

Then the solution was cooled again to 20° C.

A second 500 ml Schlenk vessel which had been repeatedly evacuated and filled with inert gas was initially charged with 150 ml of degassed n-heptane while stirring. Then it was cooled to 20° C. Thereafter, the ligand/toluene/amine solution was cautiously and gradually added dropwise to the degassed n-heptane at 20° C. while stirring within about 30 min. The precipitation of solids was perceived after about 3 min. The solids obtained were stirred at RT for another 2 h, then filtered, washed through twice with 25 ml of degassed acetone, dried.

The product was obtained in 89% yield (8.87 g).

Chlorine result according to Wickbold: 440 ppm

8) Toluene-DMAB/Acetone

In a 500 ml Schlenk vessel which had been repeatedly evacuated and filled with inert gas, 20 g of crude ligand were dissolved in 90 ml of degassed toluene and 15 ml of degassed N,N'-dimethylaminobutane at 105° C. while stirring.

Then the solution was cooled again to 20° C. A second 500 ml Schlenk vessel which had been repeatedly evacuated and filled with inert gas was initially charged with 300 ml of degassed acetone while stirring. Then it was cooled to 20° C. Thereafter, the ligand/toluene/amine solution was cautiously and gradually added dropwise to the degassed acetone at 20° C. while stirring within about 30 min. The precipitation of solids was perceived after about 45 min. The solids obtained were stirred at RT for another 3.5 h, then filtered, washed through twice with 50 ml of degassed acetone, dried.

The product was obtained in 58% yield (11.56 g).

Chlorine result according to Wickbold: 550 ppm

9) Xylene/n-Heptane

The experiment which follows was conducted analogously to the method in DE 10 2011 002 640 A1. In this case, however, crude material which had a starting chlorine value of 860 ppm total chlorine was used.

12.13 g of crude ligand were suspended in 65 ml of o-xylene and 7.5 ml of n-heptane, and heated to 100° C. Since the majority had not dissolved after 4 h, another 30 ml of o-xylene were added thereto. Then a clear solution formed. Subsequently, 35 ml of n-heptane were added and the mixture was cooled to RT overnight, in the course of which solids precipitated out. The precipitation was completed by adding a further 70 ml of n-heptane, and the solids obtained were filtered off using a G3 frit. The substance was dried for 2 h. The product was obtained in 91% yield (11.04 g).

Chlorine result according to Wickbold: 590 ppm

This experiment was conducted analogously to the abovementioned patent specification. In this case, however, only a small reduction in the chlorine value by 270 ppm was achieved. An additional factor is the very long reaction times overnight. Moreover, the precipitation of the ligand has to be completed by another addition of solvent. This is problematic especially on the industrial scale, since it is difficult to visually check complete precipitation in steel tanks.

10) Xylene/n-Heptane/Filtering Aid

The experiment which follows was conducted analogously to the method in DE 10 2011 002 640 A1. 43.2 g of crude ligand were weighed into a 1 l Schlenk, which was removed from the glove box, 260 ml of degassed o-xylene and 62 ml of degassed n-heptane were added, and the mixture was stirred at 100° C. for 1 h. In the course of this, everything dissolved. Then 8.2 g of a filtering aid based on a cellulose fibre (VITACEL® LC 200) were added, and the mixture was stirred vigorously at 100° C. for 15 min and filtered. 135 ml of degassed n-heptane were then added to the filtrate and the mixture was stirred at room temperature overnight. The next morning, 260 ml of degassed n-heptane were added to the mixture to complete the precipitation, and the mixture was stirred for 2 h. The solids were filtered off and dried. The product was obtained in 65% yield (28 g).

Chlorine result according to Wickbold: 330 ppm

The experiment was conducted analogously to the abovementioned patent specification. In addition to experiment 9), a filtering aid was also added here. Although this leads to a further reduction in the total chlorine value, it also leads to a distinct reduction in yield. This is very disadvantageous in an industrial scale synthesis, since product of value is lost here.

11)* Toluene-DMAB/Acetonitrile-DMAB

In a 500 ml Schlenk vessel which had been repeatedly evacuated and filled with inert gas, 20 of crude ligand were dissolved in 90 ml of toluene and 10 ml of N,N'-dimethylaminobutane at 105° C. while stirring. Then the solution was cooled again to RT.

A second 1 l Schlenk vessel which had been repeatedly evacuated and filled with inert gas was initially charged with 200 ml of acetonitrile and 10 ml of N,N'-dimethylaminobutane while stirring. In order to retain the suspended particles, the mixture was filtered while hot through a frit.

The precipitation of solids was perceived after about 3 min. The solids obtained were stirred at RT for another 3 h, then filtered, washed through once with 25 ml of dried acetonitrile, dried. The product was obtained in 76.5% yield (15.3 g).

Chlorine result according to Wickbold: 160 ppm

12)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 10 ml of N,N'-dimethylaminobutane at 105° C. while stirring.

A second 500 ml Schlenk vessel which had been repeatedly evacuated and filled with inert gas was initially charged with 400 ml of degassed acetonitrile and 30 ml of N,N'-dimethylaminobutane while stirring. Thereafter, the ligand/toluene/amine solution was added dropwise while still warm to the acetonitrile solution while stirring within a couple of minutes. In order to retain the suspended particles, the mixture was filtered through a frit. The precipitation of solids was perceived after about 3 min. The solids obtained were stirred at RT for another 3 h, then filtered, washed through once with 25 ml of dried acetonitrile, dried. The product was obtained in 77.5% yield.

Chlorine result according to Wickbold: 100 ppm

13)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 15 ml of N,N'-dimethylaminobutane at 105° C. while stirring.

A second 500 ml Schlenk vessel which had been repeatedly evacuated and filled with inert gas was initially charged with 300 ml of degassed acetonitrile and 15 ml of N,N'-dimethylaminobutane while stirring.

Thereafter, the ligand/toluene/amine solution was added dropwise while still very warm to the acetonitrile-amine solution while stirring within a couple of minutes. In order to retain the suspended particles, the mixture was filtered through a frit.

The precipitation of solids was perceived after about 3 min. The solids obtained were stirred at RT for another 3 h, then filtered, washed through once with 30 ml of dried acetonitrile, dried. The product was obtained in 76% yield (15.2 g).

Chlorine result according to Wickbold: 180 ppm

14)* Toluene-DMAB/Acetonitrile-DMAB

In a 500 ml Schlenk vessel which had been repeatedly evacuated and filled with inert gas, 20 g of crude ligand were in 90 ml of degassed toluene and 17.5 ml of N,N'-dimethylaminobutane at 105° C. while stirring.

A second 1000 ml Schlenk vessel which had been repeatedly evacuated and filled with inert gas was initially charged with 350 ml of degassed acetonitrile and 17.5 ml of N,N'-dimethylaminobutane while stirring.

Thereafter, the ligand/toluene/amine solution was added dropwise while hot to the acetonitrile-amine solution while stirring within a couple of minutes. In order to retain the suspended particles, the mixture was filtered through a frit.

The precipitation of solids was perceived after about 3 min. The solids obtained were stirred at RT for another 3 h, then filtered, washed through once with 25 ml of dried acetonitrile, dried. The product was obtained in 80% yield.

Chlorine result according to Wickbold: 150 ppm

15)* Toluene-DMAB/Acetonitrile-DMAB

In a 500 ml Schlenk vessel which had been repeatedly evacuated and filled with inert gas, 20 g of crude ligand were dissolved in 90 ml of toluene and 20 ml of N,N'-dimethylaminobutane at 105° C. while stirring. Then the solution was cooled again to RT.

A second 500 ml Schlenk vessel which had been repeatedly evacuated and filled with inert gas was initially charged with 400 ml of moist acetonitrile (material from drum) and 20 ml of N,N'-dimethylaminobutane while stirring. In order to retain the suspended particles, the mixture was filtered while warm through a frit.

The precipitation of solids was perceived after about 3 min. The solids obtained were stirred at RT for another 2-3 h, then filtered, washed through once with 25 ml of dried acetonitrile, dried. The product was obtained in 79.5% yield.

Chlorine result according to Wickbold: 100 ppm

This experiment shows that even water-containing solvents or precipitants can be used, and drying thereof is not absolutely necessary. In the case of phosphites, water can lead to decompositions and hence to yield losses. This is not observed here, in the case of use of water-containing solvents. This means that it is possible to dispense with an inconvenient and costly drying of the solvents.

16)* Toluene-DMAB/Acetonitrile-DMAB

In a 500 ml Schlenk vessel which had been repeatedly evacuated and filled with inert gas, 20 g of crude ligand were dissolved in 90 ml of toluene and 20 ml of N,N'-dimethylaminobutane at 108° C. while stirring. Then the solution was cooled to 90° C. within 60 min.

A second 1 l Schlenk vessel which had been repeatedly evacuated and filled with inert gas was initially charged at RT with 400 ml of acetonitrile and 20 ml of N,N'-dimethylaminobutane while stirring, and cooled to 0° C. In order to retain the suspended particles, the mixture was filtered through a frit at 90° C.

The precipitation of solids was perceived after about 1 min. The solids obtained were stirred at RT for 3 h, then filtered at RT, washed through once with 30 ml of acetonitrile, dried. The product was obtained in 83% yield (16.6 g).

Chlorine result according to Wickbold: 105 ppm

17)* Toluene-DMAB/Acetonitrile-DMAB

In a 500 ml Schlenk vessel which had been repeatedly evacuated and filled with inert gas, 20 of crude ligand were dissolved in 90 ml of degassed toluene and 20 ml of N,N'-dimethylaminobutane at 105° C. while stirring.

A second 1000 ml Schlenk vessel which had been repeatedly evacuated and filled with inert gas was initially charged with 400 ml of degassed acetonitrile and 20 ml of N,N'-dimethylaminobutane while stirring, and heated to 35° C.

Thereafter, the ligand/toluene/amine solution was added dropwise while hot to the acetonitrile-amine solution while stirring within a couple of minutes. In order to retain the suspended particles, the mixture was filtered through a frit.

The precipitation of solids was perceived after about 3 min.

The solids obtained were stirred at 35° C. for 3 h, then filtered, washed through once with 30 ml of dried acetonitrile. The product was obtained in 76.5% yield (15.3 g).

Chlorine result according to Wickbold: 90 ppm

18)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 20 ml of N,N'-dimethylaminobutane at 105° C. while stirring.

A second 1000 ml Schlenk vessel which had been repeatedly evacuated and filled with inert gas was initially charged with 400 ml of degassed acetonitrile and 20 ml of N,N'-dimethylaminobutane while stirring, and cooled to 0° C.

Thereafter, the ligand/toluene/amine solution was added dropwise at 75° C. (cooled in an oil bath) to the acetonitrile-amine solution while stirring within a couple of minutes. In order to retain the suspended particles, the mixture was filtered through a frit.

The precipitation of solids was perceived after about 3 min. The solids obtained were stirred at RT for another 3 h, then filtered, washed through once with 25 ml of dried acetonitrile, dried. The product was obtained in 84% yield (16.75 g).

Chlorine result according to Wickbold: 95 ppm

19)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 20 ml of N,N'-dimethylaminobutane at 105° C. while stirring.

The solution was subsequently cooled to 80° C. in a heating bath.

A second 1000 ml Schlenk vessel which had been repeatedly evacuated and filled with inert gas was initially charged with 400 ml of degassed acetonitrile and 20 ml of N,N'-dimethylaminobutane while stirring, and cooled to 0° C.

Thereafter, the ligand/toluene/amine solution was added dropwise at 80° C. (cooled in an oil bath) to the acetonitrile-amine solution while stirring within a couple of minutes. In order to retain the suspended particles, the mixture was filtered through a frit.

The precipitation of solids was perceived after about 3 min. The solids obtained were stirred at RT for another 3 h, then filtered, washed through once with 30 ml of dried acetonitrile, dried. The product was obtained in 81% yield (16.1 g).

Chlorine result according to Wickbold: 110 ppm

20)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 20 ml of N,N'-dimethylaminobutane at 105° C. while stirring.

The solution was subsequently cooled to 100° C. in a heating bath.

A second 1000 ml Schlenk vessel which had been repeatedly evacuated and filled with inert gas was initially charged with 400 ml of degassed acetonitrile and 20 ml of N,N'-dimethylaminobutane while stirring, and cooled to 0° C.

Thereafter, the ligand/toluene/amine solution was added dropwise at 100° C. (cooled in an oil bath) to the acetonitrile-amine solution while stirring within a couple of minutes. In order to retain the suspended particles, the mixture was filtered through a frit.

The precipitation of solids was perceived after about 3 min. The solids obtained were stirred at RT for another 4 h, then filtered, washed through once with 30 ml of dried acetonitrile, dried. The product was obtained in 82% yield (16.4 g).

Chlorine result according to Wickbold: 120 ppm

21)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 20 ml of N,N'-dimethylaminobutane at 105° C. while stirring.

The solution was subsequently cooled to 85° C. in a heating bath.

A second 1000 ml Schlenk vessel which had been repeatedly evacuated and filled with inert gas was initially charged with 400 ml of degassed acetonitrile and 20 ml of N,N'-dimethylaminobutane while stirring, and cooled to 0° C.

Thereafter, the ligand/toluene/amine solution was added dropwise at 85° C. (cooled in an oil bath) to the acetonitrile-amine solution while stirring within a couple of minutes. In order to retain the suspended particles, the mixture was filtered through a frit.

The precipitation of solids was perceived after about 3 min. The solids obtained were stirred at 0° C. for another 4 h, then filtered, washed through once with 30 ml of dried acetonitrile, dried. The product was obtained in 78% yield (15.6 g).

Chlorine result according to Wickbold: 130 ppm

22)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 20 ml of N,N'-dimethylaminobutane at 110° C. the solid while stirring.

The solution was subsequently cooled to 85° C. in a heating bath.

A second 1000 ml Schlenk vessel which had been repeatedly evacuated and filled with inert gas was initially charged with 400 ml of degassed acetonitrile and 20 ml of N,N'-dimethylaminobutane while stirring, and cooled to 0° C.

Thereafter, the ligand/toluene/amine solution was added dropwise at 85° C. (cooled in an oil bath) to the acetonitrile-amine solution while stirring within a couple of minutes. In order to retain the suspended particles, the mixture was filtered through a frit.

The precipitation of solids was perceived after about 3 min. The solids obtained were stirred at 0° C. for another 4 h, then filtered, washed through once with 30 ml of dried acetonitrile, dried. The product was obtained in 77% yield (15.4 g).

Chlorine result according to Wickbold: 110 ppm

23)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 20 ml of N,N'-dimethylaminobutane at 105° C. the solid was while stirring.

The solution was subsequently cooled to 90° C. in a heating bath.

A second 1000 ml Schlenk vessel which had been repeatedly evacuated and filled with inert gas was initially charged with 400 ml of degassed acetonitrile and 20 ml of N,N'-dimethylaminobutane while stirring, and cooled to −20° C.

Thereafter, the ligand/toluene/amine solution was added dropwise at 90° C. (cooled in an oil bath) to the acetonitrile-amine solution while stirring within a couple of minutes. In order to retain the suspended particles, the mixture was added dropwise through a frit.

The precipitation of solids was perceived after about 2 min. The solids obtained were stirred at −20° C. for another 4 h, then filtered, washed through once with 30 ml of dried acetonitrile, dried. The product was obtained in 85% yield (17 g).

Chlorine result according to Wickbold: 110 ppm

In order to prevent precipitation of the ligand out of the solvent, it has been found to be advantageous to filter the solution at a temperature of 60° C. or more, or subsequently to allow it to run into the precipitant. It is also advantageous to cool the precipitant or the mixture thereof, since this can further complete the crystallization and hence give higher yields of the product of value.

24)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 20 ml of N,N'-dimethylaminobutane at 105° C. while stirring. Then the solution was cooled again to 20° C.

A second 500 ml Schlenk vessel which had been repeatedly evacuated and filled with inert gas was initially charged with 400 ml of degassed acetonitrile and 20 ml of N,N'-dimethylaminobutane while stirring. Thereafter, the ligand/toluene/amine solution was cautiously and gradually added dropwise to the degassed acetonitrile solution at 20° C. while stirring within about 30 min.

The precipitation of solids was perceived after about 3 min. The solids obtained were stirred at RT for another 2 h, then filtered, washed through once with 25 ml of degassed acetonitrile, dried. The product was obtained in 82% yield (16.35 g).

Chlorine result according to Wickbold: 110 ppm

25)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 22.5 ml of N,N'-dimethylaminobutane at 105° C. while stirring.

A second 1000 ml Schlenk vessel which had been repeatedly evacuated and filled with inert gas was initially charged with 450 ml of degassed acetonitrile and 22.5 ml of N,N'-dimethylaminobutane while stirring.

Thereafter, the ligand/toluene/amine solution was added dropwise while still very warm to the acetonitrile-amine solution while stirring within a couple of minutes. In order to retain the suspended particles, the mixture was filtered through a frit.

The precipitation of solids was perceived after about 3 min. The solids obtained were stirred at RT for another 3 h, then filtered, washed through once with 25 ml of dried acetonitrile, dried. The product was obtained in 79.5% yield (15.9 g).

Chlorine result according to Wickbold: 180 ppm

26)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 24 ml of N,N'-dimethylaminobutane at 105° C. while stirring.

A second 500 ml Schlenk vessel which had been repeatedly evacuated and filled with inert gas was initially charged with 400 ml of degassed acetonitrile and 24 ml of N,N'-dimethylaminobutane while stirring.

Thereafter, the ligand/toluene/amine solution was added dropwise while still warm to the acetonitrile-amine solution while stirring within a couple of minutes. In order to retain the suspended particles, the mixture was filtered through a frit.

The precipitation of solids was perceived after about 3 min. The solids obtained were stirred at RT for another 2.5 h, then filtered, washed through once with 25 ml of dried acetonitrile, dried. The product was obtained in 78.5% yield (15.7 g).

Chlorine result according to Wickbold: 85 ppm

27)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 30 ml of N,N'-dimethylanninobutane at 105° C. while stirring.

A second 500 ml Schlenk vessel which had been repeatedly evacuated and filled with inert gas was initially charged with 400 ml of degassed acetonitrile and 10 ml of N,N'-dimethylaminobutane while stirring. Thereafter, the ligand/toluene/amine solution was added dropwise while still warm to the acetonitrile solution while stirring within a couple of minutes. In order to retain the suspended particles, the mixture was filtered through a frit. The precipitation of solids was perceived after about 3 min. The solids obtained were stirred at RT for another 2 h, then filtered, washed through once with 25 ml of dried acetonitrile, dried. The product was obtained in 79% yield.

Chlorine result according to Wickbold: 100 ppm

28)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 30 ml of N,N'-dimethylaminobutane at 105° C. while stirring.

A second 500 ml Schlenk vessel which had been repeatedly evacuated and filled with inert gas was initially charged with 400 ml of dried acetonitrile and 30 ml of N,N'-dimethylaminobutane while stirring. Thereafter, the ligand/toluene/amine solution was cautiously and gradually added dropwise to the dried acetonitrile solution at 20° C. while stirring within about 30 min. In order to retain the suspended particles, the mixture was filtered through a frit.

The precipitation of solids was perceived after about 3 min. The solids obtained were stirred at RT for another 2 h, then filtered, washed through once with 25 ml of dried acetonitrile, dried. The product was obtained in 79.4% yield (15.88 g).

Chlorine result according to Wickbold: 80 ppm

29)* Toluene-DMAB/Acetonitrile-DMAB

In a 500 ml Schlenk vessel which had been repeatedly evacuated and filled with inert gas, 20 g of crude ligand were dissolved in 90 ml of degassed toluene and 30 ml of N,N'-dimethylaminobutane at 105° C. while stirring.

A second 1000 ml Schlenk vessel which had been repeatedly evacuated and filled with inert gas was initially charged with 600 ml of degassed acetonitrile and 30 ml of N,N'-dimethylaminobutane while stirring.

Thereafter, the ligand/toluene/amine solution was added dropwise while hot to the acetonitrile-amine solution while stirring within a couple of minutes. In order to retain the suspended particles, the mixture was filtered through a frit.

The precipitation of solids was perceived after about 3 min. The solids obtained were stirred at RT for another 3 h, then filtered, washed through once with 25 ml of dried acetonitrile, dried. The product was obtained in 79.5% yield (15.9 g).

Chlorine result according to Wickbold: 100 ppm

30)* Toluene-DMAB/iPrOH-DMAB

In a 500 ml Schlenk vessel which had been repeatedly evacuated and filled with inert gas, 20 g of crude ligand were dissolved in 90 ml of degassed toluene and 20 ml of N,N'-dimethylaminobutane at 105° C. while stirring. Then the solution was cooled again to 20° C. After cooling, suspended particles were detected in the solution.

A second 1000 ml Schlenk vessel which had been repeatedly evacuated and filled with inert gas was initially charged with 300 ml of degassed isopropanol and 20 ml of N,N'-dimethylaminobutane while stirring. Thereafter, the ligand/toluene/amine solution was gradually filtered through a frit at 20° C. into the degassed isopropanol/amine solution while stirring within about 15 min. The precipitation of solids was perceived after about 3 min. The solids obtained were stirred at RT for another 3 h, then filtered, washed through once with 30 ml of degassed isopropanol, dried. The product was obtained in 82% yield (16.4 g).

Chlorine result according to Wickbold: 110 ppm

31)* Toluene-DMAB/iPrOH-DMAB

In a 500 ml Schlenk vessel which had been repeatedly evacuated and filled with inert gas, 20 g of crude ligand were dissolved in 90 ml of degassed toluene and 20 ml of N,N'-dimethylaminobutane at 105° C. while stirring. Then the solution was cooled again to 20° C. A second 1000 ml Schlenk vessel which had been repeatedly evacuated and filled with inert gas was initially charged with 300 ml of degassed isopropanol and 20 ml of N,N'-dimethylaminobutane while stirring. Thereafter, the ligand/toluene/amine solution was gradually filtered through a frit (removal of solid particles) at 20° C. into the degassed isopropanol/amine solution while stirring within about 15 min. The precipitation of solids was perceived after about 3 min. The solids obtained were stirred at RT for another 3 h, then filtered, washed through once with 30 ml of degassed isopropanol, dried. The product was obtained in 56% purity (11.1 g).

Chlorine result according to Wickbold: 120 ppm

32)* Toluene-Triethylamine/iPrOH-Triethylamine

In a 500 ml Schlenk vessel which had been repeatedly evacuated and filled with inert gas, 20 g of crude ligand were dissolved in 90 ml of degassed toluene and 20 ml of degassed triethylamine at 105° C. while stirring. Few suspended particles were apparent.

A 1000 ml Schlenk vessel which had been repeatedly evacuated and filled with inert gas was initially charged with 400 ml of degassed isopropanol and 20 ml of degassed triethylamine while stirring. Thereafter, the ligand/toluene/amine solution was gradually added dropwise through a frit (removal of solid particles) while warm into the degassed isopropanol/amine solution while stirring within about 15 min. The precipitation of solids was perceived after about 3 min. The solids obtained were stirred at RT for another 2 h, then filtered, washed through once with 30 ml of degassed isopropanol, dried.

The product was obtained in 84% yield (16.8 g).

Chlorine result according to Wickbold: 130 ppm

33)* Toluene-Triethylamine/Acetonitrile-Triethylamine

In a 500 ml Schlenk vessel which had been repeatedly evacuated and filled with inert gas, 50 g of crude ligand were dissolved in 225 ml of toluene and 50 ml of triethylamine at 105° C. while stirring. Then the solution was cooled.

A second 2 l Schlenk vessel which had been repeatedly evacuated and filled with inert gas was initially charged with 1000 ml of degassed acetonitrile and 50 ml of triethylamine while stirring. In order to retain the suspended particles, the mixture was filtered while warm through a frit.

The precipitation of solids was perceived after about 3 min. The solids obtained were stirred for 3 h, then filtered, washed through once with 75 ml of acetonitrile, dried. The product was obtained in 78% yield (38.9 g).

Chlorine result according to Wickbold: 95 ppm

In this case, a different base was used. Here too, very good results with respect to the chlorine value are found.

34)* Toluene-NaOMe/MeOH—NaOMe

In a 500 ml Schlenk vessel which had been repeatedly evacuated and filled with inert gas, 20 g of crude ligand were dissolved in 90 ml of degassed toluene and 1.3 ml of sodium methoxide at 105° C. and cooled. A 1000 ml Schlenk vessel which had been repeatedly evacuated and filled with inert gas was initially charged with 300 ml of degassed methanol and 1.3 ml of 30% sodium methoxide solution in methanol while stirring. Thereafter, the ligand/toluene mixture was cautiously and gradually added dropwise to the degassed methanol/sodium methoxide solution while stirring within about 30 min. In order to retain the solids fraction, the mixture was filtered through a frit. The precipitation of solids was perceived after about 3 min. The solids obtained were stirred at RT for another 2 h, then filtered, washed through twice with 25 ml of degassed methanol, dried. The product was obtained in 84% yield (16.88 g).

Chlorine result according to Wickbold: 100 ppm

35)* Toluene-NaOEt/EtOH—NaOEt

In a 500 ml Schlenk vessel which had been repeatedly evacuated and filled with inert gas, 20 g of crude ligand were dissolved in 90 ml of degassed toluene and 1.3 ml of 30% sodium ethoxide solution at 105° C. while stirring.

A 1000 ml Schlenk vessel which had been repeatedly evacuated and filled with inert gas was initially charged with 300 ml of degassed ethanol and 1.3 ml of 30% sodium ethoxide solution in ethanol while stirring. Thereafter, the ligand/toluene/sodium ethoxide solution was cautiously and gradually added dropwise while warm to the degassed ethanol/sodium methoxide solution while stirring within a couple of min. In order to retain the suspended particles, the mixture was filtered through a frit. The precipitation of solids was perceived after about 3 min. The solids obtained were stirred at RT for another 2 h, then filtered, washed through twice with 25 ml of degassed ethanol, dried. The product was obtained in 84% yield (16.7 g).

Chlorine result according to Wickbold: 90 ppm

36)* o-Xylene-DMAB/Acetonitrile-DMAB

In a 500 ml Schlenk vessel which had been repeatedly evacuated and filled with inert gas, 20 g of crude ligand were dissolved in 120 ml of degassed xylene and 15 ml of N,N'-dimethylaminobutane at 105° C. while stirring, and then cooled to 90° C. in a heating bath.

A second 1000 ml Schlenk flask which had been repeatedly evacuated and filled with inert gas was initially charged with 300 ml of degassed acetonitrile and 15 ml of N,N'-dimethylaminobutane while stirring, and cooled to 0° C.

Thereafter, the ligand/xylene solution was added dropwise at 90° C. to the acetonitrile/DMAB solution (0° C.) while stirring within a couple of minutes. In order to retain the suspended particles, the mixture was filtered through a frit.

The precipitation of solids was perceived after about 5 min. The solids obtained were stirred at 0° C. for another 4 h, then filtered, washed through three times with 30 ml of dried acetonitrile, dried. The product was obtained in 84% yield (16.6 g).

Chlorine result according to Wickbold: 65 ppm

37)* o-Xylene-DMAB/Acetonitrile-DMAB

In a 500 ml Schlenk vessel which had been repeatedly evacuated and filled with inert gas, 50 g of crude ligand were dissolved in 300 ml of degassed xylene and 50 ml of N,N'-dimethylaminobutane at 105° C. while stirring, and then cooled to 90° C. in a heating bath.

A second 2000 ml Schlenk which had been repeatedly evacuated and filled with inert gas was initially charged with 1000 ml of degassed acetonitrile and 50 ml of N,N'-dimethylaminobutane while stirring, and cooled to 0° C.

Thereafter, the ligand/xylene solution was added dropwise at 90° C. to the acetonitrile/DMAB solution (0° C.) while stirring within a couple of minutes. In order to retain the suspended particles, the mixture was filtered through a frit.

The precipitation of solids was perceived after about 5 min. The solids obtained were stirred at 0° C. for another 4 h, then filtered, washed through three times with 75 ml of degassed acetonitrile, dried.

The product was obtained in 86% yield (42.8 g).

Chlorine result according to Wickbold: 110 ppm

TABLE 1

Chlorine values

| | 1st solvent | 1st base | 2nd solvent | 2nd base | Chlorine value [ppm] |
|---|---|---|---|---|---|
| 1) | toluene | | acetonitrile | | 430 |
| 2) | toluene | | acetonitrile | triethylamine | 400 |
| 3 | toluene | | acetonitrile | DMAB | 350 |
| 4) | toluene | triethanolamine | acetonitrile | | 800 |
| 5) | toluene | triethanolamine | ethyl acetate | | >1000 |
| 6) | toluene | | EtOH | triethanolamine | 340 |
| 7) | toluene | DMAB | n-heptane | | 440 |
| 8) | toluene | DMAB | acetone | | 550 |
| 9) | xylene/n-heptane | | n-heptane | | 590 |
| 10) | xylene/n-heptane | | n-heptane | | 330 |
| 11)* | toluene | 10 ml DMAB | acetonitrile | 10 ml DMAB | 160 |
| 12)* | toluene | 10 ml DMAB | acetonitrile | 30 ml DMAB | 100 |
| 13)* | toluene | 15 ml DMAB | acetonitrile | 15 ml DMAB | 180 |
| 14)* | toluene | 17.5 ml DMAB | acetonitrile | 17.5 ml DMAB | 150 |
| 15)* | toluene | 20 ml DMAB | acetonitrile | 20 ml DMAB | 100 |
| 16)* | toluene | 20 ml DMAB | acetonitrile | 20 ml DMAB | 105 |
| 17)* | toluene | 20 ml DMAB | acetonitrile | 20 ml DMAB | 90 |
| 18)* | toluene | 20 ml DMAB | acetonitrile | 20 ml DMAB | 95 |
| 19)* | toluene | 20 ml DMAB | acetonitrile | 20 ml DMAB | 110 |
| 20)* | toluene | 20 ml DMAB | acetonitrile | 20 ml DMAB | 120 |
| 21)* | toluene | 20 ml DMAB | acetonitrile | 20 ml DMAB | 130 |
| 22)* | toluene | 20 ml DMAB | acetonitrile | 20 ml DMAB | 110 |
| 23)* | toluene | 20 ml DMAB | acetonitrile | 20 ml DMAB | 110 |
| 24)* | toluene | 20 ml DMAB | acetonitrile | 20 ml DMAB | 110 |
| 25)* | toluene | 22.5 ml DMAB | acetonitrile | 22.5 ml DMAB | 180 |
| 26)* | toluene | 24 ml DMAB | acetonitrile | 24 ml DMAB | 85 |
| 27)* | toluene | 30 ml DMAB | acetonitrile | 10 ml DMAB | 100 |
| 28)* | toluene | 30 ml DMAB | acetonitrile | 30 ml DMAB | 80 |
| 29)* | toluene | 30 ml DMAB | acetonitrile | 30 ml DMAB | 100 |
| 30)* | toluene | 20 ml DMAB | iPrOH | 20 ml DMAB | 110 |
| 31)* | toluene | 20 ml DMAB | iPrOH | 20 ml DMAB | 120 |
| 32)* | toluene | triethylamine | iPrOH | triethylamine | 130 |
| 33)* | toluene | triethylamine | acetonitrile | triethylamine | 95 |
| 34)* | toluene | NaOMe | MeOH | NaOMe | 100 |
| 35)* | toluene | NaOEt | EtOH | NaOEt | 90 |
| 36)* | o-xylene | 15 ml DMAB | acetonitrile | 15 ml DMAB | 65 |
| 37)* | o-xylene | 50 ml DMAB | acetonitrile | 50 ml DMAB | 110 |

*)inventive working examples

The invention claimed is:

1. Process for reducing the chlorine content in an organobisphosphite of one of the general formulae I, II, III, IV, V and VI:

(I)
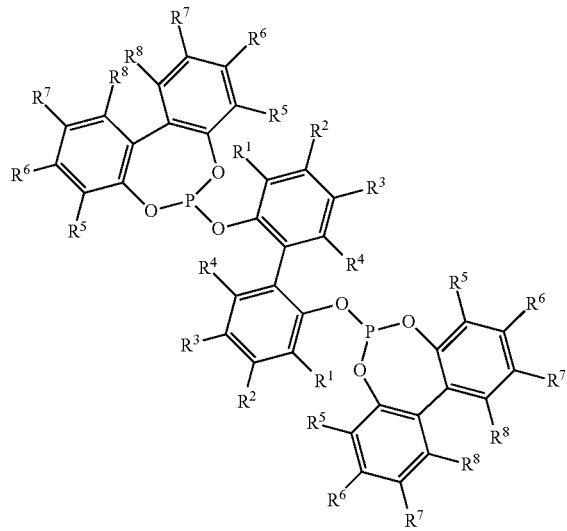
(II)
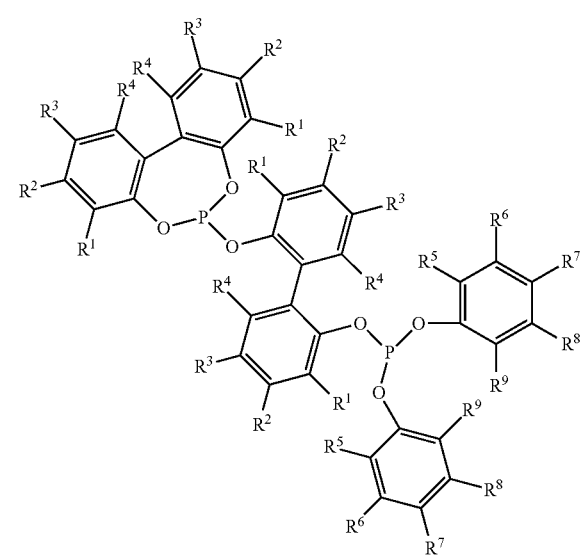
(III)
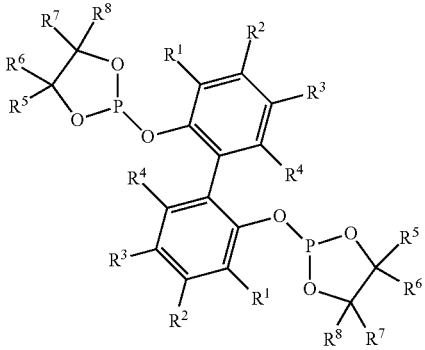
(IV)
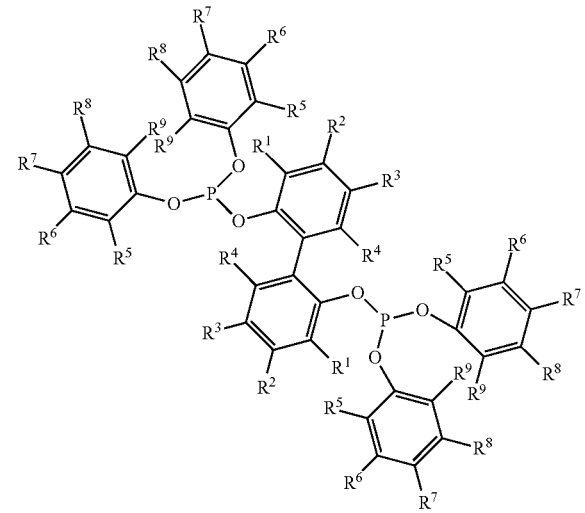
(V)
(VI)
where
R$^1$, R$^2$, R$^3$, R$^4$, R$^5$, R$^6$, R$^7$, R$^8$, R$^9$ are each independently selected from: —H, —(C$_1$-C$_{12}$)-alkyl, —O—(C$_1$-C$_{12}$)-alkyl, —O—(C$_6$-C$_{20}$)-aryl, —(C$_6$-C$_{20}$)-aryl, halogen, —COO—(C$_1$-C$_{12}$)-alkyl, —CONH—(C$_1$-C$_{12}$)-alkyl, —(C$_6$-C$_{20}$)-aryl-CON[(C$_1$-C$_{12}$)-alkyl]$_2$, —CO—(C$_1$-

$C_{12}$)-alkyl, —CO—($C_6$-$C_{20}$)-aryl, —COOH, —OH, —$SO_3H$, —$SO_3Na$, —$NO_2$, —CN, —$NH_2$, —N[($C_1$-$C_{12}$)-alkyl]$_2$;

and the four following pairs of radicals are not both the same radical in all four pairs:

$R^1$ and $R^5$, $R^2$ and $R^6$, $R^3$ and $R^7$, $R^4$ and $R^8$;

comprising the process steps of:

a) partly or fully dissolving the organobisphosphite in a first solution, b) introducing the first solution into a second solution, which results in precipitation of the purified organobisphosphite, wherein the first solution comprises a first solvent and a first base, the second solution comprises a second solvent and a second base, and the first solvent is selected from:

aromatics, alcohols, acetone, ethyl acetate, acetonitrile, ethers, the second solvent is selected from:

aromatics, C5-C10-alkanes, alcohols, acetone, ethyl acetate, acetonitrile, ethers, the first base is selected from:

amine bases, alkoxides, pyridine, pyridine derivatives, N-methyl-2-pyrrolidone, triethanolamine, the second base is selected from:

amine bases, alkoxides, pyridine, pyridine derivatives, N-methyl-2-pyrrolidone, triethanolamine, and the organobisphosphite has better solubility in the first solvent than in the second solvent.

2. Process according to claim 1, wherein the first solvent is selected from: ethyl acetate, anisole, ortho-xylene, toluene, acetone, methanol, ethanol, propanol, isopropanol, acetonitrile.

3. Process according to claim 1, wherein the second solvent is selected from: ethyl acetate, anisole, ortho-xylene, toluene, acetone, methanol, ethanol, propanol, isopropanol, acetonitrile, tetrahydrofuran, diethyl ether, glycol, C5-C10-alkanes.

4. Process according to claim 1, wherein the first base is selected from: triethylamine, dimethylaminobutane, pentylamine, hexylamine, dibutylamine, N-methyl-2-pyrrolidone, triethanolamine, sodium methoxide, sodium ethoxide, pyridine, dimethylaminopyridine.

5. Process according to claim 1, wherein the second base is selected from: triethylamine, dimethylaminobutane, pentylamine, hexylamine, dibutylamine, N-methyl-2-pyrrolidone, triethanolamine, sodium methoxide, sodium ethoxide, pyridine, dimethylaminopyridine.

6. Process according to claim 1, wherein the second solution comprises a third solvent non-identical to the second solvent.

7. Process according to claim 6, wherein the third solvent is selected from: aromatics, alcohols, acetone, ethyl acetate, acetonitrile, ethers.

8. Process according to claim 1, wherein the organobisphosphite is dissolved fully in the first solution in process step a).

9. Process according to claim 1, wherein the first base and the second base are not the same base.

10. Process according to claim 1, wherein the organobisphosphite has a chlorine content of 1500 ppm to 100 000 ppm on introduction in process step b).

11. Process according to claim 1, wherein the second solution is heated to a temperature in the range from −20° C. to 120° C. before the first solution is introduced into the second solution in process step b).

12. Process according to claim 1, wherein the organobisphosphite has one of the general formulae I, II, IV and VI:

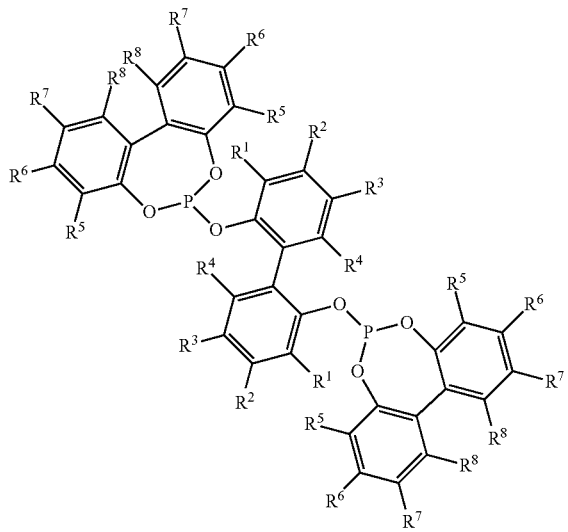

(I)

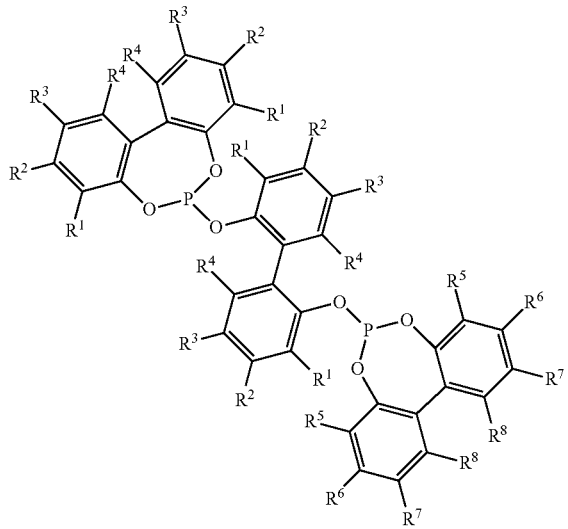

(II)

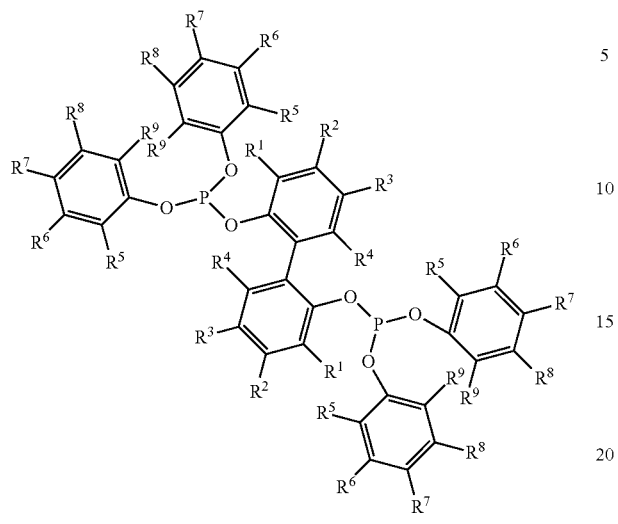
(IV)
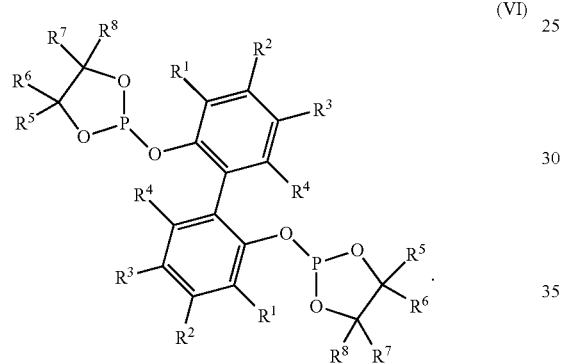
(VI)
13. Process according to claim 1,
wherein the organobisphosphite has one of the general formulae I, II and VI:
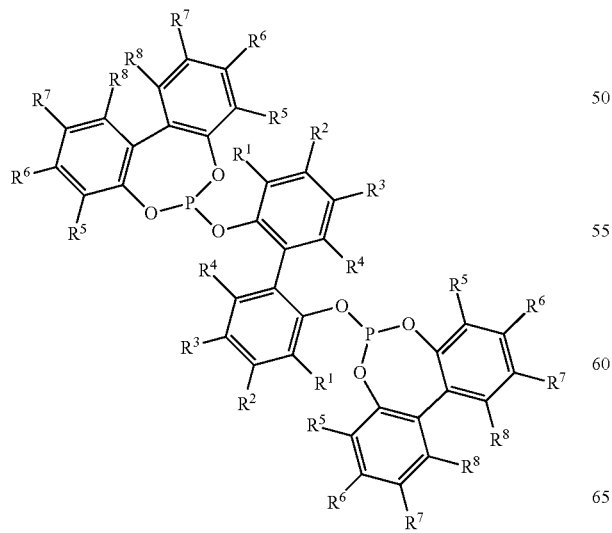
(I)
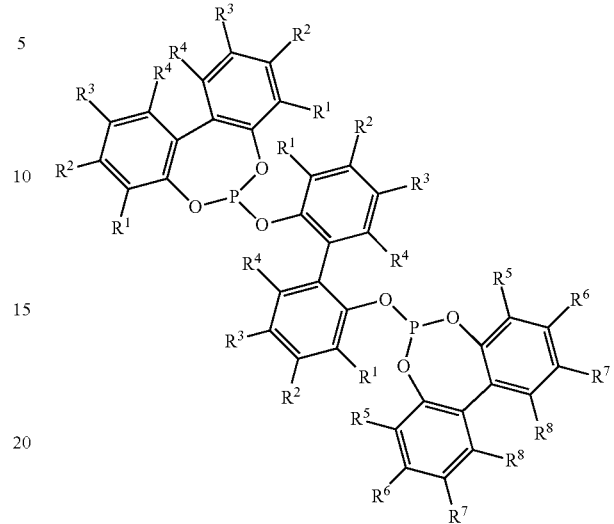
(II)
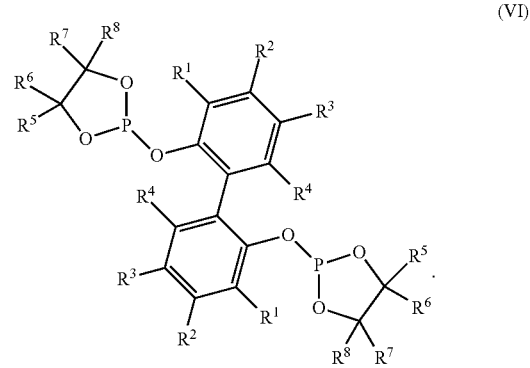
(VI)
14. Process according to claim 1,
wherein the organobisphosphite has one of the general formulae I, II and VI:
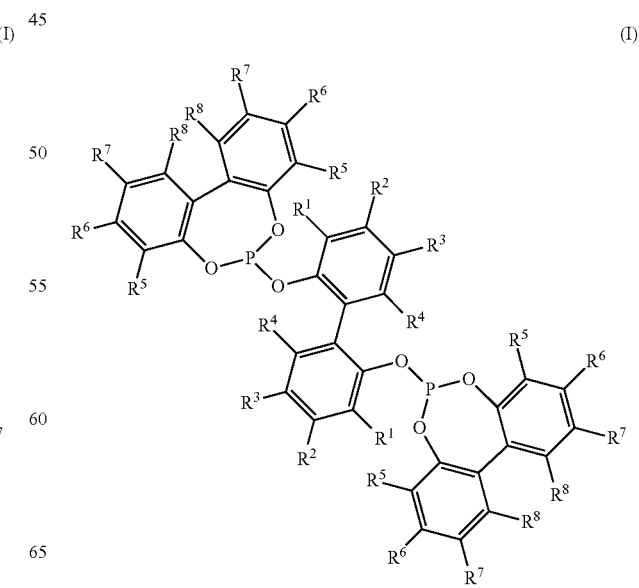
(I)

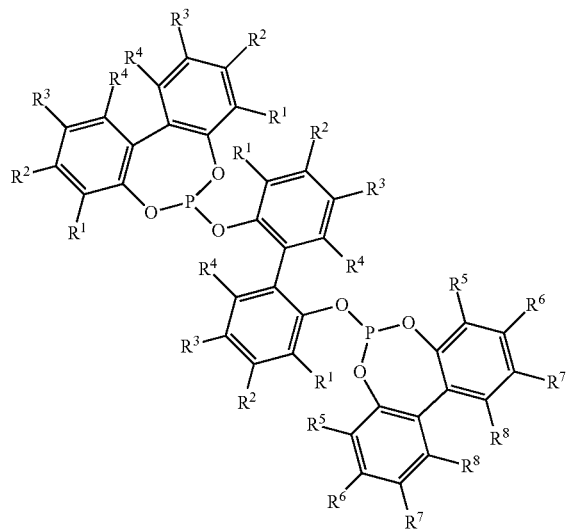
(II)
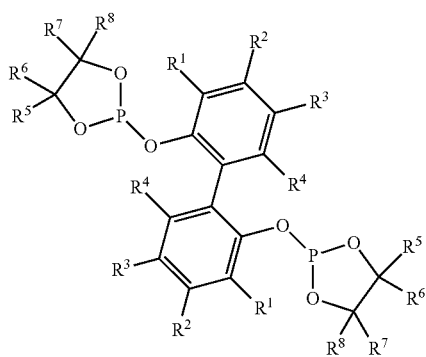
(VI)
and where
R$^1$, R$^2$, R$^3$, R$^4$, R$^5$, R$^6$, R$^7$, R$^8$ are each independently selected from: —H, —(C$_1$-C$_{12}$)-alkyl, —O—(C$_1$-C$_{12}$)-alkyl, —O—(C$_6$-C$_{20}$)-aryl, —(C$_6$-C$_{20}$)-aryl.
* * * * *